United States Patent
Kato et al.

(10) Patent No.: US 7,946,987 B2
(45) Date of Patent: May 24, 2011

(54) ULTRASONIC DIAGNOSTIC APPARATUS

(75) Inventors: Makoto Kato, Kanagawa (JP); Yoshinao Tan-naka, Kanagawa (JP); Hisashi Hagiwara, Kanagawa (JP); Takao Suzuki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 567 days.

(21) Appl. No.: 11/995,993

(22) PCT Filed: Jul. 20, 2006

(86) PCT No.: PCT/JP2006/314427
§ 371 (c)(1),
(2), (4) Date: Jan. 17, 2008

(87) PCT Pub. No.: WO2007/011000
PCT Pub. Date: Jan. 25, 2007

(65) Prior Publication Data
US 2009/0118615 A1 May 7, 2009

(30) Foreign Application Priority Data
Jul. 20, 2005 (JP) ................................ 2005-210233

(51) Int. Cl.
*A61B 8/00* (2006.01)
(52) U.S. Cl. ...................................................... 600/438
(58) Field of Classification Search .......... 600/437–438, 600/443, 447, 450, 485–486, 490–495, 513, 600/587
See application file for complete search history.

(56) References Cited

U.S. PATENT DOCUMENTS

| | | | | |
|---|---|---|---|---|
| 5,601,084 A | * | 2/1997 | Sheehan et al. | 600/450 |
| 5,840,028 A | * | 11/1998 | Chubachi et al. | 600/437 |
| 6,165,128 A | * | 12/2000 | Cespedes et al. | 600/463 |
| 6,237,398 B1 | * | 5/2001 | Porat et al. | 73/54.09 |
| 7,043,063 B1 | | 5/2006 | Noble et al. | |
| 7,261,694 B2 | * | 8/2007 | Torp et al. | 600/443 |
| 7,318,804 B2 | * | 1/2008 | Weitzel et al. | 600/438 |
| 7,338,452 B2 | * | 3/2008 | Shiina et al. | 600/467 |

(Continued)

FOREIGN PATENT DOCUMENTS
JP 10005226 1/1998
(Continued)

OTHER PUBLICATIONS

Hiroshi Kanai et al, Elasticity Imaging of Atheroma With Transcutaneous Ultrasound, Circulation, 203, pp. 3018-3021.

(Continued)

*Primary Examiner* — Francis Jaworski
(74) *Attorney, Agent, or Firm* — Pearne & Gordon LLP

(57) ABSTRACT

The present invention aims at providing an ultrasonic diagnostic apparatus capable of displaying a stable spatial distribution of elastic characteristics for each heart beat without depending on the measurement of blood pressure and the accuracy or stability of such measurement, where an ultrasonic wave transmitted from an ultrasonic probe 13 and reflected by biomedical tissue is input to a computing section 19 by way of a receiving section 15, a delay time control section 16, phase detection section 17 and filter section 18. In accordance with the phase detection signal acquired from the phase detection section 17, the computing section 19 computes a relative elastic characteristic which is an elastic characteristic normalized by an elastic characteristic of an arbitrary reference area in the biomedical tissue. A distribution of relative elastic characteristics computed by the computing section is displayed on a display section 21.

12 Claims, 6 Drawing Sheets

U.S. PATENT DOCUMENTS

| | | | | |
|---|---|---|---|---|
| 7,369,691 B2 * | 5/2008 | Kondo et al. | | 382/128 |
| 7,404,798 B2 * | 7/2008 | Kato et al. | | 600/450 |
| 7,727,153 B2 * | 6/2010 | Fritz et al. | | 600/449 |
| 7,744,537 B2 * | 6/2010 | Kanai et al. | | 600/453 |
| 2007/0232883 A1 * | 10/2007 | Ilegbusi | | 600/407 |
| 2008/0214961 A1 * | 9/2008 | Matsumoto et al. | | 600/587 |
| 2009/0216123 A1 * | 8/2009 | Matsumura et al. | | 600/443 |
| 2009/0318806 A1 * | 12/2009 | Kanai et al. | | 600/443 |

FOREIGN PATENT DOCUMENTS

| | | |
|---|---|---|
| JP | 2003508139 | 3/2003 |
| WO | 2006011504 | 2/2006 |

OTHER PUBLICATIONS

International Search Report, Oct. 24, 2006.

\* cited by examiner

ULTRASONIC DIAGNOSTIC APPARATUS

TECHNICAL FIELD

The present invention relates to an ultrasonic diagnostic apparatus for measuring a character of a tissue in a living body, more particularly, an elastic characteristic of a vascular wall tissue.

BACKGROUND ART

The number of patients suffering from circulatory diseases, such as cardiac infarction or brain infarction, is increasing recently, and prevention and treatment of these diseases has posed a big problem.

Arterial sclerosis has a close relationship with the onset of cardiac infarction and brain infarction. Specifically, when an atheroma is formed on an arterial wall or when new cells of an arterial wall are created for various reasons, such as high blood pressure, the artery loses elasticity, to thus become hard and fragile. As a result of a blood vessel being closed at a position where the atheroma is formed or a vascular tissue covering the atheroma becoming ruptured, the atheroma flows into the blood vessel, to thus close another location of the artery or rupture a hardened region of the artery. In this way, the diseases are induced. Therefore, early diagnosis of arterial sclerosis becomes important for prevention or treatment of these diseases.

Manifestation of arterial sclerosis has recently been diagnosed by means of direct observation of an internal state of the blood vessel through use of a vessel catheter. However, this diagnosis involves a problem of a necessity for insertion of a vessel catheter into a blood vessel, thereby imposing heavy load on a subject. Therefore, observation involving the use of the vessel catheter is employed for a subject who is sure to have a lesion into which arterial sclerosis has developed, to thus locate the lesion. This method has never been used as; for example, a test for health care.

Measurement of a cholesterol level, which is one cause of arterial sclerosis, or a blood pressure level is a test which imposes a small burden on the subject and which can be practiced readily. However, these values do not directly indicate the degree of arterial sclerosis.

So long as arterial sclerosis can be early diagnosed and a therapeutic medicine for arterial sclerosis can be administered to the subject, the medicine becomes effective for treatment of arterial sclerosis. Once arterial sclerosis has progressed, further progress of arterial sclerosis can be inhibited by the therapeutic medicine. However, complete recovery of a hardened artery is said to be difficult to be made.

For these reasons, there has been sought a diagnostic method or a diagnostic apparatus which diagnoses arterial sclerosis in its early stage with involvement of a small burden on the subject before it progresses.

In the meantime, an ultrasonic diagnostic apparatus and an X-ray diagnostic apparatus have heretofore been used as a noninvasive medical diagnostic apparatus which imposes a small burden on the subject. Geometrical information about the inside of a body or information about a chronological change in the internal shape of the body can be acquired without causing pain in the subject by radiation of an ultrasonic wave or an X ray onto the body from the outside. As a result of acquisition of the information about a chronological change in the shape of an object of measurement in the body (i.e., motion information), information about the character of the object of measurement can be obtained. Specifically, an elastic characteristic of the blood vessel in the body can be determined, and the degree of arterial sclerosis can be ascertained directly. In particular, when compared with the X-ray diagnosis, the ultrasonic diagnosis enables performance of measurement by means of bringing an ultrasonic probe into contact with the subject. Accordingly, the ultrasonic diagnosis is superior because it obviates a necessity for administration of a contrast medium or a risk of X-ray exposure.

Recent advancement of electronics technology enables remarkable enhancement of the accuracy of measurement of the ultrasonic diagnostic apparatus. In association with this, development of an ultrasonic diagnostic apparatus which measures micromotion of biomedical tissue is in progress. For instance, use of a technique described in Patent Document 1 enables high-precision measurement of a vibrational component of vasomotion whose amplitude is of several microns and which is as fast as several hundreds of hertz, and hence high-precision measurement of a change in the thickness of the vascular wall or the distortion of the wall to an order of microns is reported to become practicable.

Patent Document 1 discloses a technique for noninvasively measuring a waveform of motion speed of each location in biomedical tissue through use of an ultrasonic wave, thereby determining an elastic modulus of a microarea. Since use of a tissue tracking technique described in Patent Document 1 enables high-precision measurement of vasomotion, a chronological change h(t) in the thickness of an arterial wall can be measured high accuracy. Provided that the thickness of the arterial wall acquired at the time of measurement of low blood pressure is "h"; that the maximum amount of change in the thickness of the arterial wall acquired in one cardiac cycle is Δh; and that pulse pressure is Δp, a radial elastic modulus E of an arterial wall is determined as follows:

$$E = \Delta p \cdot h / \Delta h \quad \text{(Eq. 1)}$$

Use of such a high-precision measurement technique enables detailed measurement of a two-dimensional distribution of elastic characteristics of the arterial wall. For instance, Non-Patent Document 1 describes an example illustration showing a two-dimensional distribution of elastic modulus of a carotid arterial wall superimposed on a B-mode tomogram. The degree of hardness of the arterial wall is not uniform, and the hardness of the arterial wall is present in the form of a certain distribution. Accurately grasping a localized distribution of elastic modulus, which is a feature quantity representing the degree of hardness of an artery, is important for diagnosing arterial sclerosis.

Patent Document 1: JP-A-10-5226

Non-Patent Document 1: Hiroshi Kanai et al., "Elasticity Imaging of Atheroma With Transcutaneous Ultrasonic Preliminary Study," Circulation, Vol. 107, pp. 3018 to 3021, 2003.

DISCLOSURE OF THE INVENTION

Problem that the Invention is to Solve

However, the disclosed technique encounters a problem provided below. In order to determine the elastic modulus E of the arterial wall as indicated by (Eq. 1), the pulse pressure Δp must be measured. Although an elastic modulus determined from the maximum amount of change in thickness achieved during one cardiac cycle can be measured once in one cardiac cycle, actual blood pressure slightly changes for each heart beat. In order to determine a more accurate elastic modulus, pulse pressure must be measured once in one cardiac cycle. However, a commonly-used intermittent method, typified by a cuff-type sphygmomanometer, cannot determine pulse pressure for each heart beat. Moreover, since a blood flow of the subject is temporarily closed by the cuff-type blood pressure measurement method, the method is unsuitable for long hours of use. Further, according to a continuous method, typified by a tonometer capable of measuring blood pressure for each heart beat, pulse pressure can be measured for each heart beat. However, additional equipment is required, which in turn complicates measurement of an elastic modulus. Another problem of an increase in burden imposed on the subject is also encountered.

In light of the above, the present invention aims at providing an ultrasonic diagnostic apparatus capable of displaying a stable spatial distribution of elastic characteristics for each heart beat without depending on the accuracy and stability of measurement of blood pressure and without involvement of measurement of blood pressure.

Means for Solving the Problem

An ultrasonic diagnostic apparatus of the present invention includes:

a transmission section for driving an ultrasonic probe for transmitting an ultrasonic transmission wave to biomedical tissue;

a receiving section which amplifies a reflected ultrasonic wave acquired as a result of reflection of the ultrasonic transmission wave from the biomedical tissue and received by the ultrasonic probe, to thus generate a received signal;

a phase detection section for subjecting the received signal to phase detection;

a computing section which determines an amount of change in thickness arising at a plurality of positions within the biomedical tissue from a phase detection signal acquired from the phase detection section and which computes a relative elastic characteristic from a value determined by dividing a maximum amount of change in thickness acquired from an arbitrary reference area in the biomedical tissue by a maximum amount of change in thickness acquired from another area; and a display section for displaying a distribution of the relative elastic characteristics computed by the computing section. According to the present invention, an accurate, stable distribution of elastic characteristics can be determined without measuring pulse pressure of a subject at all.

An ultrasonic diagnostic apparatus of the present invention includes:

a transmission section for driving an ultrasonic probe for transmitting an ultrasonic transmission wave to biomedical tissue;

a receiving section which amplifies a reflected ultrasonic wave acquired as a result of reflection of the ultrasonic transmission wave from the biomedical tissue and received by the ultrasonic probe, to thus generate a received signal;

a phase detection section for subjecting the received signal to phase detection;

a computing section which determines distortions appearing at a plurality of positions within the biomedical tissue from a phase detection signal acquired from the phase detection section and which computes a relative elastic characteristic from a value determined by dividing distortion arising in an arbitrary reference area in the biomedical tissue by a distortion appearing in another area; and a display section for displaying a distribution of the relative elastic characteristics computed by the computing section. According to the present invention, an accurate, stable distribution of elastic characteristics can be determined without measuring pulse pressure of a subject at all.

An ultrasonic diagnostic apparatus of the present invention includes:

a transmission section for driving an ultrasonic probe for transmitting an ultrasonic transmission wave to biomedical tissue;

a receiving section which amplifies a reflected ultrasonic wave acquired as a result of reflection of the ultrasonic transmission wave from the biomedical tissue and received by the ultrasonic probe, to thus generate a received signal;

a phase detection section for subjecting the received signal to phase detection;

a computing section which determines elastic characteristics of a plurality of positions within the biomedical tissue from a phase detection signal acquired from the phase detection section and which computes a relative elastic characteristic from a value determined by dividing an elastic characteristic of another area by an elastic characteristic of an arbitrary reference area in the biomedical tissue; and a display section for displaying a distribution of the relative elastic characteristics computed by the computing section. According to the present invention, an accurate, stable distribution of elastic characteristics can be determined without depending on the accuracy of measurement of blood pressure of the subject.

In the ultrasonic diagnostic apparatus of the present invention, the computing section has a reference area setting section for setting the reference area. According to the present invention, an arbitrary area in a spatial elastic characteristic distribution image can be designated, to thus take the designated area as a reference area used for computing a relative elastic characteristic.

In the ultrasonic diagnostic apparatus, the display section displays the reference area set by the computing section so as to be superimposed on at least one of an ultrasonic tomogram image or an elastic characteristic image. According to the present invention, the reference area can be ascertained without fail, and a diagnosis based on the distribution of elastic characteristics can be performed easily.

In the ultrasonic diagnostic apparatus, the display section displays positional coordinates of the reference area set by the computing section in the form of numerals. According to the present invention, the reference area can be ascertained without fail, and a diagnosis based on the distribution of elastic characteristics can be performed easily.

As mentioned above, an ultrasonic diagnostic apparatus of the present invention includes a transmission section for driving an ultrasonic probe for transmitting an ultrasonic transmission wave to biomedical tissue; a receiving section which amplifies a reflected ultrasonic wave acquired as a result of reflection of the ultrasonic transmission wave from the biomedical tissue and received by the ultrasonic probe, to thus generate a received signal; a phase detection section for subjecting the received signal to phase detection; a computing section for computing a relative elastic characteristic, which is a normalized elastic characteristic, from a phase detection signal acquired from the phase detection section; and a display section for displaying a distribution of the relative elastic characteristics computed by the computing section.

According to the present invention, a stable spatial distribution of elastic characteristics can be displayed for each heart beat without depending on the accuracy and without involvement of measurement of blood pressure.

Advantage of the Invention

According to the present invention, an arbitrary area in a spatial elastic characteristic distribution image is designated, and another elastic characteristic is computed as an elastic characteristic ratio while an elastic characteristic value of the area or an average of elastic characteristics is taken as a reference, and the thus-computed ratio is displayed as a spatially-distributed image. As a result, there can be embodied an ultrasonic diagnostic apparatus capable of displaying a stable spatial distribution of elastic characteristics for each heart beat without depending on the accuracy and stability of measurement of blood pressure and without involvement of measurement of blood pressure.

DESCRIPTIONS OF THE REFERENCE NUMERALS

1 EXTRAVASCULAR TISSUE
2 BODY SURFACE
3 BLOOD VESSEL
4 VASCULAR ANTERIOR WALL
5 BLOOD
11 ULTRASONIC DIAGNOSTIC APPARATUS
12 SPHYGMOMANOMETER
13 ULTRASONIC PROBE
14 TRANSMISSION SECTION
15 RECEIVING SECTION
16 DELAY TIME CONTROL SECTION
17 PHASE DETECTION SECTION
18 FILTER SECTION
19 COMPUTING SECTION
20 COMPUTED DATA STORAGE SECTION
21 DISPLAY SECTION
22 ELECTROCARDIOGRAPH
31 REFERENCE AREA SETTING SECTION
32 ELASTIC CHARACTERISTIC COMPUTING SECTION
33 RELATIVE ELASTIC CHARACTERISTIC COMPUTING SECTION
41 REGION OF INTEREST
42 ADVENTITIA
43 INTIMA-MEDIA COMPLEX
44 REFERENCE AREA
60 LIVING BODY
62 BIOMEDICAL TISSUE
63 VASCULAR WALL
64 BLOOD
66 ACOUSTIC LINE
67 ULTRASONIC BEAM

Embodiments of the present invention will be described hereunder by reference to the drawings.

First Embodiment

Figure 1:
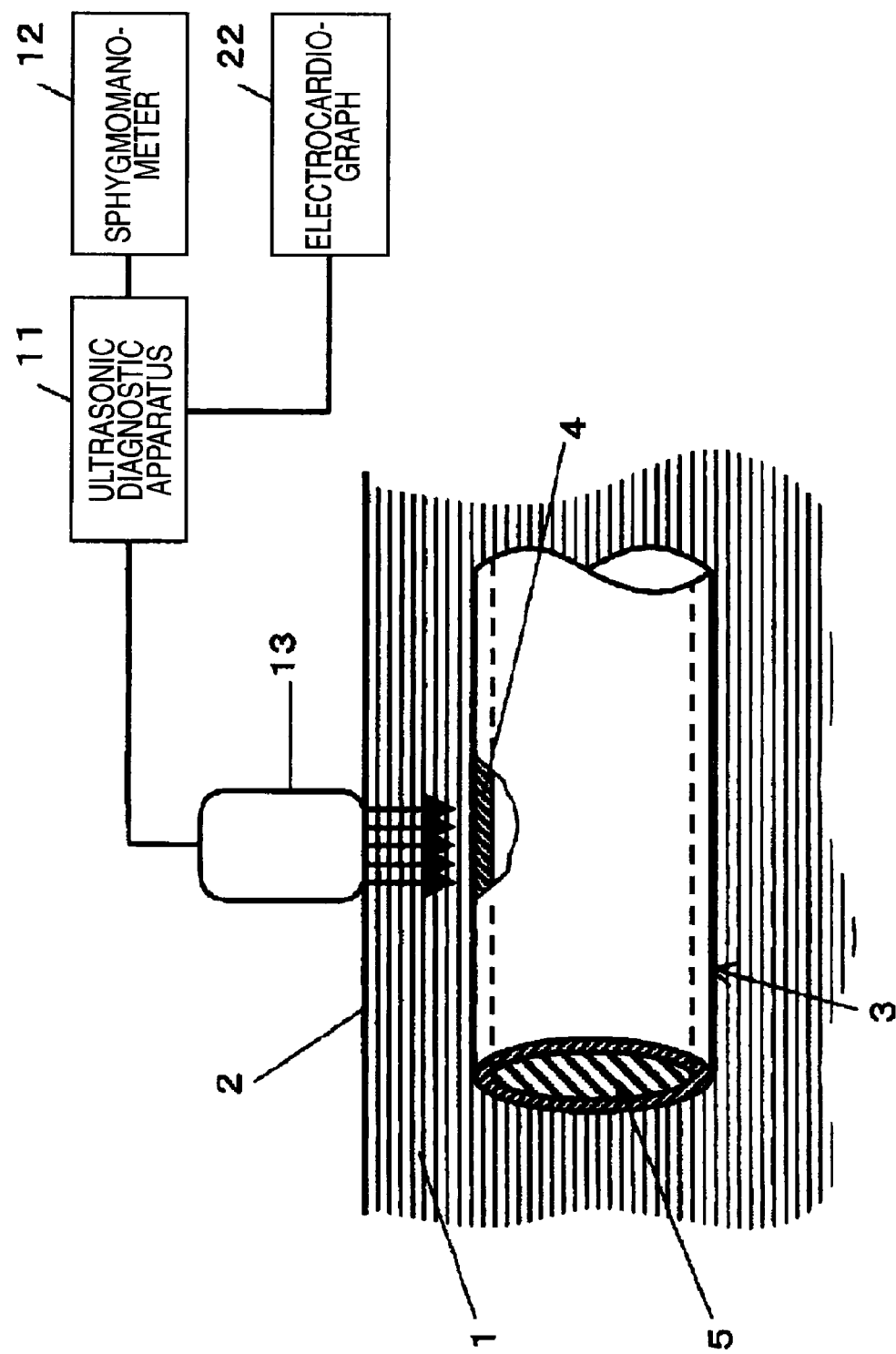
FIG. 1 is a view showing a state achieved when a character of a vascular wall tissue is diagnosed by use of an ultrasonic diagnostic apparatus of a first embodiment of the present invention.

FIG. 1 is a view showing a state achieved when a character of a vascular wall tissue is diagnosed by use of an ultrasonic diagnostic apparatus 11 of a first embodiment of the present invention. An ultrasonic probe 13 connected to the ultrasonic diagnostic apparatus 11 is set so as to come into intimate contact with a body surface 2 of a subject and transmits an ultrasonic wave into an extra vascular tissue 1. The transmitted ultrasonic wave undergoes reflection and scattering on a blood vessel and blood 5; a portion of reflected and scattered waves returns to the ultrasonic probe 13; and the thus-returned wave is received as an echo (a reflected ultrasonic wave). The ultrasonic diagnostic apparatus 11 analyzes and computes a received signal, to thus determine geometrical information and motion information about a vascular anterior wall 4. The ultrasonic diagnostic apparatus 11 is also connected to a sphygmomanometer 12 and an electrocardiograph 22, and blood pressure data pertaining to the subject measured by the sphygmomanometer 12 and an electrocardiographic waveform measured by the electrocardiograph 22 are input to the ultrasonic diagnostic apparatus 11.

According to a method described in; for example, Patent Document 1, the ultrasonic diagnostic apparatus 11 uses both an amplitude and a phase of a detection signal acquired by detection of a received ultrasonic wave signal, thereby determining an instantaneous position of an object by means of a limited least square method. The thickness of a microarea in the vascular anterior wall 4 and the amount of a chronological change in thickness can be measured with sufficient accuracy by means of high-precision phase tracking (the measurement accuracy of an amount of positional change is ±0.2 microns). Moreover, an elastic characteristic of the microarea in the vascular anterior wall 4 by use of the blood pressure data acquired from the sphygmomanometer 12. Further, the electrocardiographic waveform measured by the electrocardiograph 22 is used as a trigger signal for determining timing for acquisition of data or resetting data. The electrocardiograph 22 can be replaced with a cardiometer or an arterial pulse wave detector which serves as another biomedical signal detection means, and a cardiac sound waveform or an arterial pulse waveform can also be used in place of the electrocardiographic waveform. Moreover, use of a waveform pertaining to the amount of motion or a waveform pertaining to the amount of change in thickness, which is measured by the ultrasonic diagnostic apparatus 11, obviates a necessity for inputting a trigger signal from the outside.

Figure 2:
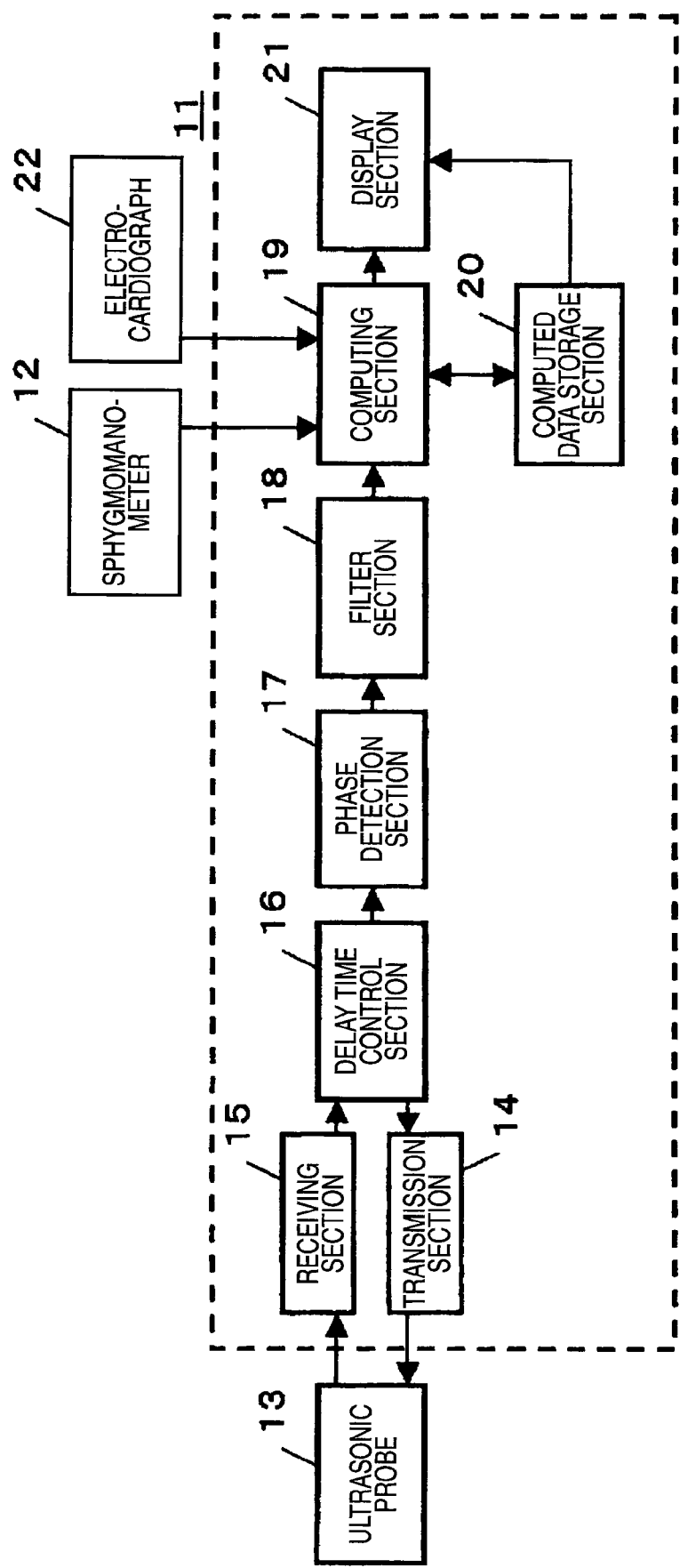
FIG. 2 is a block diagram showing the configuration of the ultrasonic diagnostic apparatus of the first embodiment of the present invention.

The configuration and operation of the ultrasonic diagnostic apparatus 11 will now be described in detail. FIG. 2 is a block diagram showing the configuration of the ultrasonic diagnostic apparatus 11. The ultrasonic diagnostic apparatus 11 has a transmission section 14, a receiving section 15, a delay time control section 16, a phase detection section 17, a filter section 18, a computing section 19, a computed data storage section 20, and a display section 21. These sections are controlled by means of an unillustrated computer.

The transmission section 14 generates a predetermined drive pulse signal which drives the ultrasonic probe 13, and outputs the thus-generated signal to the ultrasonic probe 13. An ultrasonic transmission wave transmitted from the ultrasonic probe 13 driven by the drive pulse signal undergoes reflection and scattering on biomedical tissue, such as the blood vessel 3, and a resultantly-reflected ultrasonic wave is received by the ultrasonic probe 13. The frequency of the drive pulse used for generating an ultrasonic wave is determined such that a preceding ultrasonic pulse and a subsequent ultrasonic pulse, which are adjacent to each other along a time axis, do not overlap each other, in consideration of the depth of an object of measurement and the acoustic velocity of the ultrasonic wave.

The receiving section 15 amplifies the reflected ultrasonic wave received by the ultrasonic probe 13, to thus generate a received signal. The receiving section 15 includes an amplification section and an A/D conversion section (neither of these sections are illustrated); amplifies the reflected ultrasonic wave; and converts the amplified wave further into a digital signal. The transmission section 14 and the receiving section 15 are built from an electronic component or the like.

The delay time control section 16 is connected to the transmission section 14 and the receiving section 15, and controls a delay time of a drive pulse signal imparted from the transmission section 14 to a group of ultrasonic transducers of the ultrasonic probe 13. As a result, the direction of an acoustic line of an ultrasonic beam of the ultrasonic transmission wave transmitted from the ultrasonic probe 13 and a focal depth of the ultrasonic beam are changed. An aperture diameter or the position of a focal point can be changed by means of controlling the delay time of the received signal which is received by the ultrasonic probe 13 and which is generated by the receiving section 15. An output from the delay time control section 16 is input to the phase detection section 17.

The phase detection section 17 subjects the received signal delay-controlled by the delay time control section 16 to phase detection, thereby generating a phase detection signal including an actual-section signal and an imaginary-section signal. The phase detection signal is input to a filter section 18. The filter section 18 eliminates high-frequency components, components reflected from substances other than the object of measurement, noise components, and the like. The phase detection section 17 and the filter section 18 can also be formed from software or hardware.

Figure 3:
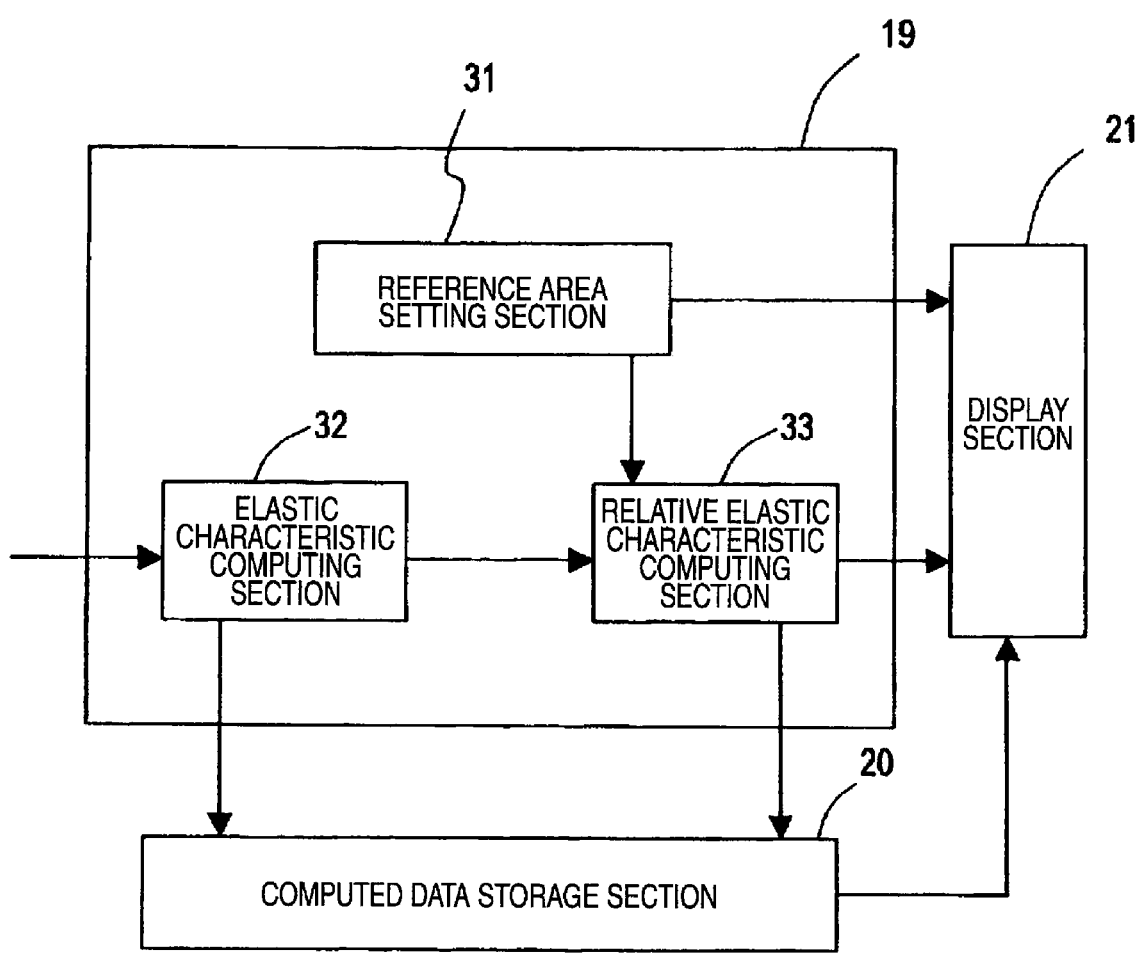
FIG. 3 is a block diagram showing, in detail, the configuration of a computing section in the ultrasonic diagnostic apparatus of the first embodiment of the present invention.

The actual-section signal and the imaginary-section signal of the phase detection signal passed through the filter section 18 are input to the computing section 19. FIG. 3 is a block diagram showing a detailed configuration of the computing section 19. The computing section 19 includes a reference area setting section 31, an elastic characteristic computing section 32, and a relative elastic characteristic computing section 33. The computing section 19 can also be formed from software or hardware.

The elastic characteristic computing section 32 computes, from the actual-section signal and the imaginary-section signal of the phase detection signal, the motion speed of the biomedical tissue achieved at a plurality of points of measurement and integrates the motion speed, thereby determining the amount of movement (chronological displacements of respective points of measurement). The amount of change in the thickness of the biomedical tissue (the amount of expansion and contraction) among the points of measurement is determined from the thus-determined amount of movement. Information about one cardiac cycle is received from the electrocardiograph 22, the maximum amount of change in thickness—a difference between the maximum amount of change in thickness and the minimum amount of change in thickness acquired during one cardiac cycle—and the maximum thickness are determined. Distortion of the biomedical tissue is determined from the maximum amount of change in thickness and the maximum thickness, and an elastic characteristic of the biomedical tissue located between the respective points of measurement is determined by use of blood pressured at a acquired from the sphygmomanometer 12.

The thus-determined elastic characteristic of the biomedical tissue is mapped in correspondence to a measurement area, and the mapping is output to the display section 21 as a spatially-distributed image acquired during each cardiac cycle. When an operator of the ultrasonic diagnostic apparatus 11 has not caused the reference area setting section 31 to set a reference area, the relative elastic characteristic computing section 33 performs no processing. Processing performed when the reference area setting section 31 is caused to set a reference area will be described later.

Figure 4:
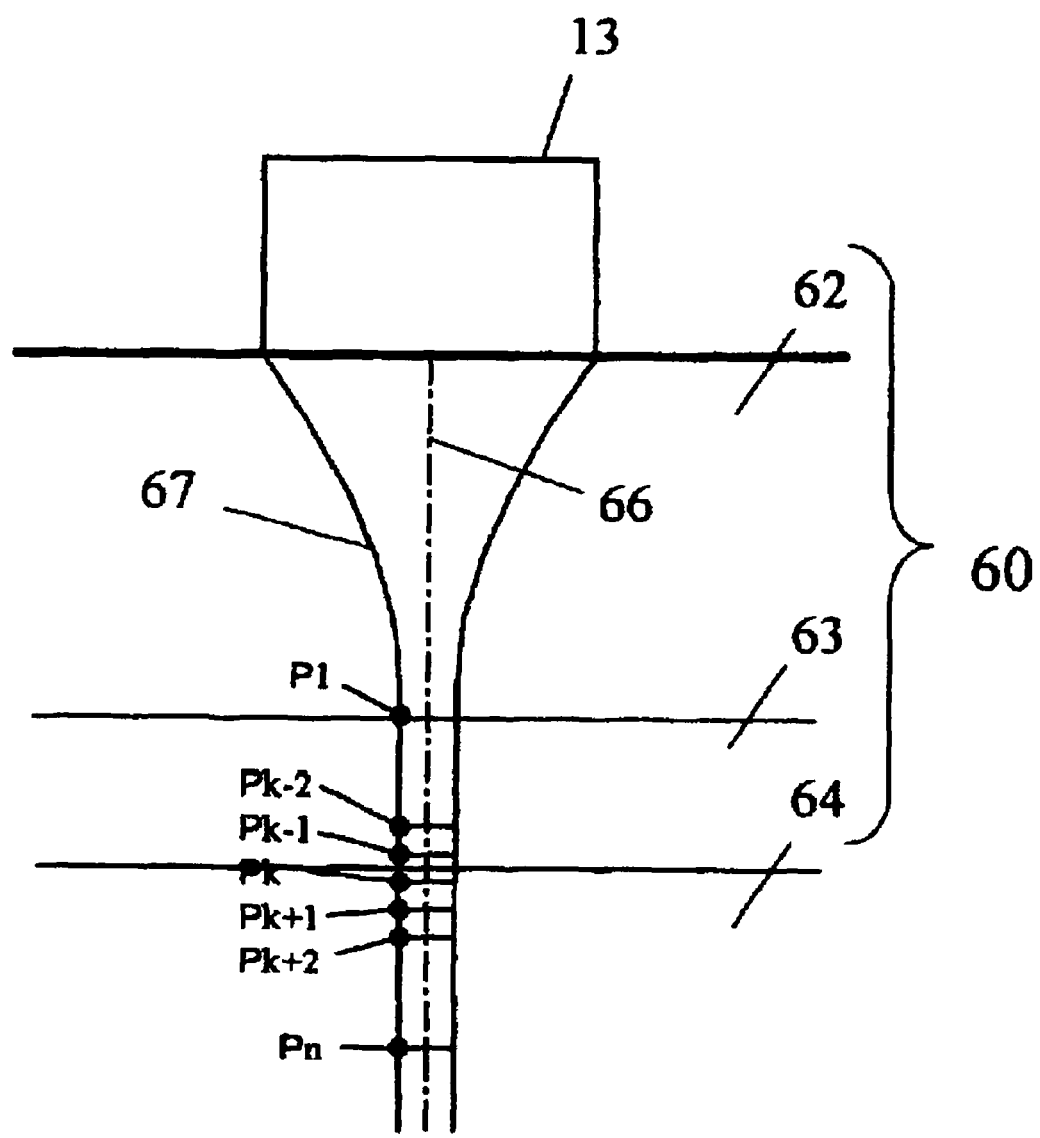
FIG. 4 is a view schematically showing an ultrasonic beam propagating through a living body when the character of the vascular wall tissue is diagnosed by use of the ultrasonic diagnostic apparatus of the first embodiment of the present invention.

These computing operations performed by the computing section 19 will be described in a further detailed manner by reference to FIGS. 4 and 5. FIG. 4 schematically shows an ultrasonic beam 67 propagating through a living body 60. FIG. 4 shows biomedical tissue 62, a vascular wall 63, and blood 64 other than the blood vessel. An ultrasonic transmission wave transmitted from the ultrasonic probe 13 located on the surface of the living body 60 propagates through the living body 60. The ultrasonic transmission wave propagates through the living body 60 as the ultrasonic beam 67 having a certain finite width. During the course of propagation of the beam, the ultrasonic beam undergoes reflection or scattering on the vascular wall 63, the blood 64, and the like, and a portion of the reflected or scattered ultrasonic wave returns to the ultrasonic probe 13 and is received as a reflected ultrasonic wave. The reflected ultrasonic wave is detected as a discrete time-series signal $r_k(t)$. As the reflected time-series signal is acquired from a tissue closer to the ultrasonic probe 13, the signal is located closer to the point of origin along the time axis. The width (beam size) of the ultrasonic beam 67 can be controlled by means of changing a delay time.

At the time of commencement of measurement, a plurality of points of measurement $P_n$ ($P_1, P_2, P_3, \ldots, P_k, \ldots, P_n$, where "n" is a natural number of three or more) located along an acoustic line 66 that is a center axis of the ultrasonic beam are arranged at given intervals L in sequence of $P_1, P_2, P_3, \ldots, P_k, \ldots, P_n$ from the ultrasonic probe 13. The phase detection section 17 subjects the reflected wave signal $r_k(t)$ to orthogonal detection by use of a predetermined detection frequency, thereby determining a detection signal $R_k(t)$ consisting of an actual-section signal and an imaginary-section signal, and the thus-determined signal is caused to pass through the filter section 18. Under the constraint that the amplitude of the detection signal $R_k(t)$ and the amplitude of a detection signal $R_k(t+\Delta t)$ acquired after elapse of a minute time $\Delta t$ remain unchanged and that only the phase of the signal and a reflection point change, the elastic characteristic computing section 32 of the computing section 19 performs correlation computation of the detection signal $R_k(t)$ and $R_k(t+\Delta t)$, and a correlation signal $Q_k(t)$ of the position $P_k$ is determined by (Eq. 2).

$$Q_k(t)=R_k(t+\Delta t)\times R_k^*(t) \text{ (* designates a complex conjugate)} \quad \text{(Eq. 2)}$$

An angle $\theta_k(t)$ formed from an actual section and an imaginary section of the correlation signal $Q_k(t)$ is determined, and a chronological change in a point of measurement $P_k$; that is, the amount of movement $h_k(t)$ of the position $P_k$, is determined from the angle $\theta_k(t)$.

Figure 5:
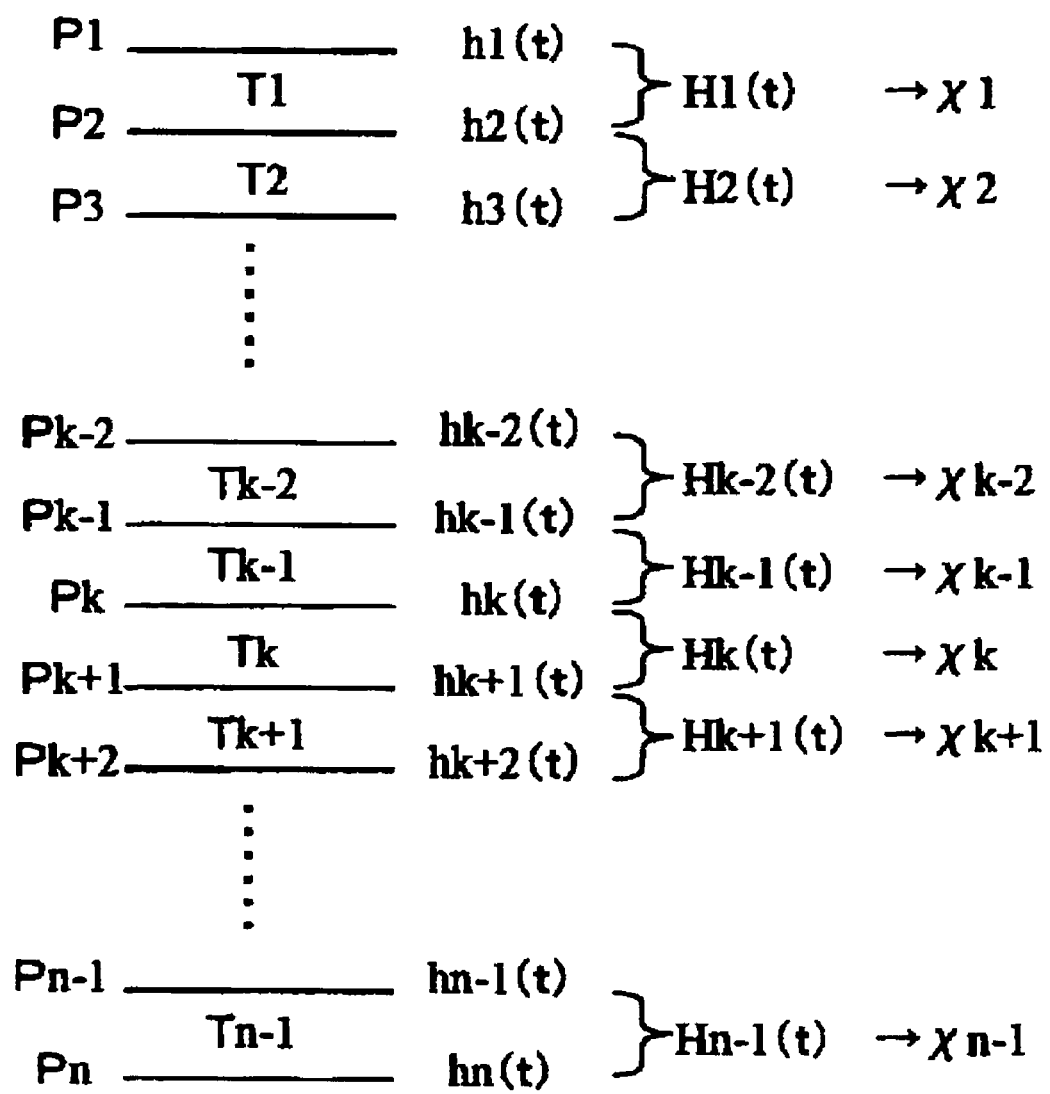
FIG. 5 is a view showing a relationship between a position of measurement and a tissue, which is an object to be subjected to computation of an elastic characteristic, when the character of the vascular wall tissue is diagnosed by use of the ultrasonic diagnostic apparatus of the first embodiment of the present invention.

FIG. 5 shows a relationship between the point of measurement $P_n$ and tissue $T_n$ which is an object of elastic characteristic computation. The tissue $T_n$ is situated at a position sandwiched between adjacent points of measurement $P_k$ and $P_{k+1}$ while assuming a thickness L. (n−1) target tissues $T_1 \ldots T_{n-1}$ are defined on the basis of "n" points of measurement $P_1 \ldots P_n$.

An amount of change $H_k(t)$ which is the amount of expansion and contraction of the target tissue $T_k$ is determined as $H_k(t)=h_{k+1}(t)-h_k(t)$ from the points of measurement $P_k$ and $P_{k+1}$ and amounts of movement $h_k(t)$ and $h_{k+1}(t)$.

A change in the thickness of the tissue $T_k$ of the vascular wall 63 arises according to a change in blood pressure caused by a heart rate and is iterated essentially in synchronism with the cardiac cycle. Consequently, the elastic characteristic is preferably determined as a numeral for each cardiac cycle in synchronism with the cardiac cycle. The maximum value and the minimum value are extracted from the amount of change $H_k(t)$ in thickness achieved during one cardiac cycle, and a difference between the maximum value and the minimum value is taken as the maximum amount of change in thickness $\Delta H_k$. A difference between the maximum blood pressure and the minimum blood pressure is taken as pulse pressure $\Delta p$. When the maximum value (or an initial value) of the thickness of the target tissue is taken as $H_m$, $H_m$ is expressed as $L\times\{(k+1)-k\}=L$, and hence a distortion $s_k$ and an elastic characteristic $\chi_k$ can be determined by (Eq. 3) and (Eq. 4).

$$S_k=\Delta H_k/H_m=\Delta H_k/L \quad \text{(Eq. 3)}$$

$$\chi_k=\Delta_p/S_k=\Delta_p\cdot H_m/\Delta H_k \quad \text{(Eq. 4)}$$

The number of points of measurement Pn and an interval between the points of measurement can be set arbitrarily in accordance with a characteristic of living tissue which is an objective of measurement or a target of measurement.

The following problem exists in the elastic characteristic which is determined by the above-mentioned method and which is displayed on the display section 21. The elastic characteristic is determined by means of dividing the pulse pressure $\Delta_p$ by the distortion $S_k$, and pulse pressure must be measured for each heart beat in order to determine an accurate elastic characteristic. In general, many subjects have essentially-constant pulse pressure. Handling the pulse pressure measured immediately before measurement of an elastic characteristic as being non-changing for several minutes to several tens of minutes is very preferable in terms of ease of measurement. However, for instance, when the pulse pressure of the subject is unstable for each heart beat, measurement of pulse pressure for each heart beat is required. Use of a tonometer, or the like, enables measurement of pulse pressure measured for each heart beat, but raises a problem of a necessity for another device or complication of a measurement system.

Figure 6:
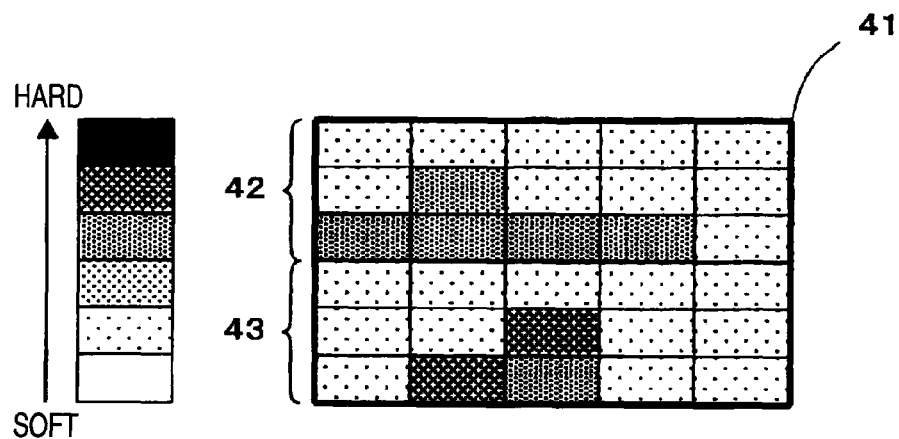
FIG. 6 is a view schematically showing an example distribution of elastic characteristics in a region of interest achieved when the region of interest is set in a portion of a vascular wall in a case where the character of the vascular wall tissue is diagnosed by use of the ultrasonic diagnostic apparatus of the first embodiment of the present invention.

A technique for solving the problem will be described in detail hereunder. FIG. 6 is a view schematically showing the distribution of elastic characteristics in the region of interest when the region of interest 41 is set in a portion on the vascular wall. The region of interest 41 is set so as to simultaneously include an adventitia 42 of the vascular wall and an intima-media complex 43, and elastic characteristic values of respective microareas determined by the computing section 19 are coded according to a preset color scheme, whereby a spatially-distributed image is formed.

Figure 7:
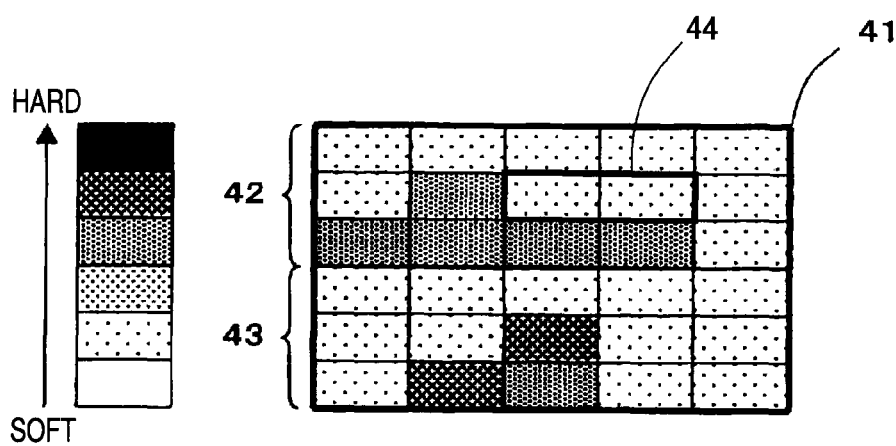
FIG. 7 is a view schematically showing an example of setting, in the distribution of elastic characteristics in the region of interest, a reference area defining an area where an elastic characteristic serving as a reference is to be determined, when the character of the vascular wall tissue is diagnosed by use of the ultrasonic diagnostic apparatus of the first embodiment of the present invention.

FIG. 7 is a view schematically showing that a reference area 44 defining an area where an elastic characteristic taken as a reference is set in the distribution of elastic characteristics shown in FIG. 6. The operator of the ultrasonic diagnostic apparatus 11 can arbitrarily determine the size and position of the reference area 44. Specifically, it is desirable that the reference area should be set at a position on the adventitia 42 or in the intima-media complex 43 of the subject which has been diagnosed by the operator as a healthy area. Although the reference area 44 is set on the adventitia 42 in FIG. 7, the reference area 44 may also be provided on the intima-media complex 43. The elastic characteristic values achieved within the reference area 44 are averaged, and a resultant average is taken as a reference elastic characteristic $\chi s$.

Figure 8:
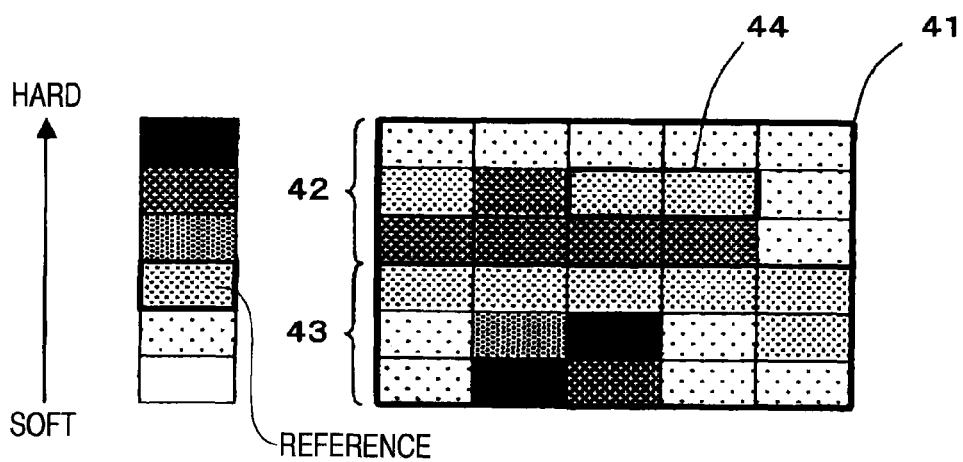
FIG. 8 is a view schematically showing an example distribution of a relative elastic characteristic which is determined by normalization of respective elastic characteristics in the region of interest through use of the reference elastic characteristic, when the character of the vascular wall tissue is diagnosed by use of the ultrasonic diagnostic apparatus of the first embodiment of the present invention.

FIG. 8 is a view schematically showing the distribution of relative elastic characteristics determined by normalization (normalizing operation) of the respective elastic characteristics acquired within the region of interest 41 by means of the reference elastic characteristic $\chi_s$. Arbitrary elastic characteristics $\chi_k$ acquired within the region of interest 41 are divided by the reference elastic characteristic $\chi_s$. Namely, $\chi_k/\chi_s$ is determined, and a result is taken as a relative elastic characteristic $\chi_k'$. The respective relative elastic characteristics $\chi_k'$ are coded in accordance with a predetermined color scheme, to thus generate a spatially-distributed image. So long as the same pulse pressure $\Delta_p$ is used for determining the reference elastic characteristic $\chi_s$ and the elastic characteristic $\chi_k$, the influence of the pulse pressure $\Delta_p$ is canceled during computation of the relative characteristic $\chi_k'=\chi_k/\chi_s$. Resultantly, the relative elastic characteristic $\chi_k'$ does not depend on a change or error in pulse pressure $\Delta_p$, and a relative distribution of hardness and softness compared with the healthy area can be determined accurately, stably.

Operation of the ultrasonic diagnostic apparatus 11 performed when the relative elastic characteristic is determined will be described by reference to FIG. 3. The operator finds a healthy area from an image pertaining to the distribution of elastic characteristics appearing on the display section 21, and activates the reference area setting section 41, to thus set the reference area 44 such as that shown in FIG. 7. Setting is performed by way of an interface section (not shown) of the ultrasonic diagnostic apparatus 11. The reference area setting section 31 sends reference area information specified by the operator to the relative elastic characteristic computing section 33. The relative elastic characteristic computing section 33 first determines an elastic characteristic $\chi_s$ in the reference area by use of the elastic characteristic $\chi_k$ sent from the elastic characteristic computing section 32, and subsequently determines the relative elastic characteristic $\chi_k'$. The relative elastic characteristic $\chi_k'$ is output as a spatially-distributed image to the display section 21, as well as being stored in the computed data storage section 20. It is desirable that the reference area setting section 31 should send the reference position information to the display section 21 so that the operator can set the reference area 44 at an arbitrary position while viewing the display section 21, to thus display the reference position information. Now, although a display of the reference area 44 is preferably displayed so as to be superimposed on a B-mode tomogram or an elastic characteristic image, positional coordinates of the reference area 44 may also be displayed as numerals.

As mentioned above, even when the pulse pressure of the subject is unstable or measurement of pulse pressure performed for each heart beat is inaccurate, an accurate, stable distribution of elastic characteristics can be determined by performing computation described in connection with the embodiment for each heart beat. Moreover, an accurate, stable distribution of elastic characteristics can be determined without measurement of pulse pressure for each heart beat.

Although the relative elastic characteristic is determined as $\chi_k' = \chi_k/\chi_s$ in the present embodiment, it may also be possible to arbitrarily set a constant A and a constant B provided that $\chi_k' = A \times (\chi_k/\chi_s) + B$, so long as the setting falls within the scope of gist of the present invention.

It is desirable that the reference area 44 should be set in the middle of measurement of an elastic characteristic. However, even when data stored in the computed data storage section 20 are read after completion of measurement, to thus display an image, and when setting is performed in that state, an analogous advantage is yielded.

It is desirable that the reference area 44 should be set manually by way of the interface section of the ultrasonic diagnostic apparatus 11 after the operator has determined whether or not tissue is healthy. However, for instance, an adventitia located in the region of interest 41 may be extracted by means of an automatic adventitia extraction function, and the thus-extracted membrane may also be set as the reference area 44.

Moreover, when the operator has determined that a healthy area is not present within the region of interest 41, an elastic characteristic of the same area acquired in the past or an elastic characteristic of another region (a region other than the region of interest 41) may also be used. In this case, however, a difference exists between the times when the areas which are objects of comparison have been measured, and hence attention must be paid to the possibility of occurrence of a change in pulse pressure.

Second Embodiment

A second embodiment of the present invention will now be described. The ultrasonic diagnostic apparatus of the second embodiment has the analogous structure and function as the structure and function of the ultrasonic diagnostic apparatus 11 of the first embodiment excluding the function of the computing section 19. The same reference numerals are used unless otherwise particularly explained.

As described in connection with the first embodiment, the computing section 19 first determines the amount of change in thickness $H_k(t)$ of a plurality of micro-biomedical tissues $T_k$ which are objects of measurement, and determines the maximum amount of change $\Delta H_k$ in thickness from the thus-determined amount of change. Next, a distortion $S_k$ is computed from the maximum thickness (or initial value) $H_m$ and $\Delta H_k$ of the target tissue, thereby computing the elastic characteristic $\chi_k$ from the distortion $S_k$ and the pulse pressure $\Delta_p$. A relative elastic characteristic $\chi_k' = \chi_k/\chi_s$ by use of the predetermined reference elastic characteristic $\chi_s$.

The relative elastic characteristic $\chi_k'$ can also be determined as shown in (Eq. 5), provided that an average value of distortion acquired in the reference area 44 is taken as reference distortion $S_s$.

$$\chi_k' = \chi_k/\chi_s = (\Delta p/S_k)/(\Delta p/S_s) = S_s/S_k \qquad \text{(Eq. 5)}$$

(Eq. 5) shows that the pulse pressure $\Delta p$ does not need to be measured during computation of the relative elastic characteristic $\chi_k'$. Specifically, even in the case of a subject who has unstable pulse pressure $\Delta_p$ and when the pulse pressure $\Delta_p$ is not measured at all, an accurate, stable distribution of relative elastic characteristics can be determined.

Moreover, the relative elastic characteristic $\chi_k'$ can also be expressed as (Eq. 6) when an average of amounts of maximum changes in thickness acquired within the reference area 44 is taken as a reference maximum thickness change level $\Delta H_s$.

$$\chi_k' = S_s/S_k = (\Delta H_s/H_m)/(\Delta H_s/H_m) = \Delta H_s/\Delta H_k \qquad \text{(Eq. 6)}$$

Although, in the present embodiment, the relative elastic characteristic $\chi_k'$ is determined by use of (Eq. 5) and (Eq. 6), $\chi_k'' = A \times \chi_k' + B$ (A and B are constants which are arbitrarily set) may also be computed, to thus utilize $\chi_k''$, so long as utilization of $\chi_k''$ falls within the scope of gist of the present invention. In particular, the elastic characteristic $\chi_k$ can be determined without determination of the elastic characteristic $\chi_k$ by means of using the reference elastic characteristic $\chi_s$ for the constant A and 0 for the constant B, so long as the maximum amount of change in thickness $\Delta H_k$ and the distortion $S_k$ are determined. The reference elastic characteristic $\chi s$ may also be an actually-measured value or a general value, or the like, acquired from an area, such as an adventitia, where an individual different is less likely to arise.

As described above, computation described in connection with the second embodiment is performed for each hear beat, whereby an accurate, stable distribution of elastic characteristics can be measured without measuring pulse pressure of the subject at all.

Although the present invention has been described in detail by reference to the specific embodiments, it is manifest to persons skilled in the art that the present invention is susceptible to various alterations or modifications without departing from the spirit and scope of the present invention.

The present invention is based on Japanese Patent Application (JP-A-2005-210233) filed on Jul. 20, 2005 in Japan, the contents of which are hereby incorporated by reference.

INDUSTRIAL APPLICABILITY

The ultrasonic diagnostic apparatus of the present invention can be utilized for an ultrasonic diagnostic apparatus, or the like, capable of displaying a stable spatial distribution of elastic characteristics for each hear beat without depending on the accuracy or stability of measurement of blood pressure and without involvement of measurement of blood pressure.

The invention claimed is:

1. An ultrasonic diagnostic apparatus for diagnosing a blood vessel by an ultrasonic wave, comprising:
   a transmission section for driving an ultrasonic probe for transmitting an ultrasonic transmission wave to the blood vessel, wherein the ultrasonic probe is a body surface scanning probe;
   a receiving section which amplifies a reflected ultrasonic wave acquired as a result of reflection of the ultrasonic transmission wave from the blood vessel and received by the ultrasonic probe, to thus generate a received signal;
   a phase detection section for subjecting the received signal to phase detection;
   a computing section which determines amounts of change in thicknesses, due to pulse pressure from a cardiac cycle, respectively arising at a plurality of positions within a wall of the blood vessel from a phase detection signal acquired from the phase detection section and which computes a relative elastic characteristic, which is a normalized elastic characteristic, from a value determined by dividing a maximum amount of change in thickness, due to the pulse pressure from the cardiac cycle, acquired from an arbitrary reference area in the wall of the blood vessel by a maximum amount of change in thickness, due to the pulse pressure from the cardiac cycle, acquired from another area in the wall of the blood vessel and outside of the arbitrary reference area; and a display section for displaying a distribution of the relative elastic characteristics computed by the computing section, wherein the maximum amount of change in thickness acquired from the arbitrary reference area in the wall of the blood vessel is selectable from a maximum amount of change in thickness acquired from an area of an adventitia in the blood vessel or a maximum amount of change in thickness acquired from a healthy vessel tissue reference area from the past.

2. The ultrasonic diagnostic apparatus according to claim 1, wherein the computing section has a reference area setting section for setting the reference area.

3. The ultrasonic diagnostic apparatus according to claim 2, wherein the display section displays the reference area set by the computing section so as to be superimposed on at least one of an ultrasonic tomogram image or an elastic characteristic image.

4. The ultrasonic diagnostic apparatus according to claim 2, wherein the display section displays positional coordinates of the reference area set by the computing section in the form of numerals.

5. An ultrasonic diagnostic apparatus for diagnosing a blood vessel by an ultrasonic wave, comprising:
a transmission section for driving an ultrasonic probe for transmitting an ultrasonic transmission wave to the blood vessel, wherein the ultrasonic probe is a body surface scanning probe;
a receiving section which amplifies a reflected ultrasonic wave acquired as a result of reflection of the ultrasonic transmission wave from the blood vessel and received by the ultrasonic probe, to thus generate a received signal;
a phase detection section for subjecting the received signal to phase detection;
a computing section which determines distortions, due to pulse pressure from a cardiac cycle, respectively appearing at a plurality of positions within a wall of the blood vessel from a phase detection signal acquired from the phase detection section and which computes a relative elastic characteristic, which is a normalized elastic characteristic, from a value determined by dividing distortion, due to the pulse pressure from the cardiac cycle, arising in an arbitrary reference area in the wall of the blood vessel by a distortion, due to the pulse pressure from the cardiac cycle., appearing in another area in the wall of the blood vessel and outside of the arbitrary reference area; and
a display section for displaying a distribution of the relative elastic characteristics computed by the computing section, wherein the distortion arising in the arbitrary reference area is selectable from a distortion arising in an area of an adventitia in the blood vessel or a distortion acquired from a healthy vessel tissue reference area from the past.

6. The ultrasonic diagnostic apparatus according to claim 5, wherein the computing section has a reference area setting section for setting the reference area.

7. The ultrasonic diagnostic apparatus according to claim 6, wherein the display section displays the reference area set by the computing section so as to be superimposed on at least one of an ultrasonic tomogram image or an elastic characteristic image.

8. The ultrasonic diagnostic apparatus according to claim 6, wherein the display section displays positional coordinates of the reference area set by the computing section in the form of numerals.

9. An ultrasonic diagnostic apparatus for diagnosing a blood vessel by an ultrasonic wave, comprising:
a transmission section for driving an ultrasonic probe for transmitting an ultrasonic transmission wave to the blood vessel, wherein the ultrasonic probe is a body surface scanning probe;
a receiving section which amplifies a reflected ultrasonic wave acquired as a result of reflection of the ultrasonic transmission wave from the blood vessel and received by the ultrasonic probe, to thus generate a received signal;
a phase detection section for subjecting the received signal to phase detection;
a computing section which determines elastic characteristics of a plurality of positions within a wall of the blood vessel from a phase detection signal acquired from the phase detection section and which computes a relative elastic characteristic, which is a normalized elastic characteristic, from a value determined by dividing an elastic characteristic of another area in the wall of the blood vessel by an elastic characteristic of an arbitrary reference area in the wall of blood vessel, wherein the another area in the wall of the blood vessel is outside of the arbitrary reference area; and
a display section for displaying a distribution of the relative elastic characteristics computed by the computing section, wherein the elastic characteristic of the arbitrary reference area within the wall of blood vessel is selectable from an elastic characteristic of an area of an adventitia in the blood vessel or an elastic characteristic acquired from a healthy vessel tissue reference area from the past.

10. The ultrasonic diagnostic apparatus according to claim 9, wherein the computing section has a reference area setting section for setting the reference area.

11. The ultrasonic diagnostic apparatus according to claim 10, wherein the display section displays the reference area set by the computing section so as to be superimposed on at least one of an ultrasonic tomogram image or an elastic characteristic image.

12. The ultrasonic diagnostic apparatus according to claim 10, wherein the display section displays positional coordinates of the reference area set by the computing section in the form of numerals.

* * * * *

UNITED STATES PATENT AND TRADEMARK OFFICE
CERTIFICATE OF CORRECTION

| | |
|---|---|
| PATENT NO. | : 7,946,987 B2 |
| APPLICATION NO. | : 11/995993 |
| DATED | : May 24, 2011 |
| INVENTOR(S) | : Makoto Kato et al. |

It is certified that error appears in the above-identified patent and that said Letters Patent is hereby corrected as shown below:

On the front page of the patent, under "Other Publications", line 2, please delete "203", and insert therefore --2003--

Signed and Sealed this
Twenty-second Day of November, 2011

David J. Kappos
*Director of the United States Patent and Trademark Office*